(12) United States Patent
Long et al.

(10) Patent No.: US 8,343,480 B2
(45) Date of Patent: Jan. 1, 2013

(54) ADMINISTRATION OF STEM OR PROGENITOR CELLS TO A JOINT TO ENHANCE RECOVERY FROM JOINT SURGERY

(75) Inventors: Marc Long, Denville, NJ (US); Lin Song, Wayne, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 385 days.

(21) Appl. No.: 12/617,042

(22) Filed: Nov. 12, 2009

(65) Prior Publication Data

US 2010/0150888 A1 Jun. 17, 2010

Related U.S. Application Data

(60) Provisional application No. 61/199,242, filed on Nov. 14, 2008.

(51) Int. Cl.
*A01N 63/00* (2006.01)
(52) U.S. Cl. ...................... 424/93.2; 424/93.1
(58) Field of Classification Search ............... None
See application file for complete search history.

(56) References Cited

U.S. PATENT DOCUMENTS

| | | | |
|---|---|---|---|
| 5,486,359 A | 1/1996 | Caplan et al. | |
| 7,311,905 B2 | 12/2007 | Hariri | |
| 7,485,629 B2 | 2/2009 | Marcum | |
| 7,790,458 B2 | 9/2010 | Xu et al. | |
| 2002/0005205 A1 | 1/2002 | Barry et al. | |
| 2003/0031695 A1 | 2/2003 | Kadiyala et al. | |
| 2003/0032179 A1* | 2/2003 | Hariri | 435/366 |
| 2004/0048372 A1 | 3/2004 | Hariri | |
| 2005/0089578 A1 | 4/2005 | Werkmeister et al. | |
| 2005/0260251 A1 | 11/2005 | Hiltner et al. | |
| 2007/0059823 A1 | 3/2007 | Verfaillie et al. | |
| 2007/0264238 A1 | 11/2007 | Shaw et al. | |
| 2008/0131410 A1 | 6/2008 | Hariri | |
| 2010/0172885 A1 | 7/2010 | Pittenger et al. | |

FOREIGN PATENT DOCUMENTS

WO 2005105121 A1 11/2005

OTHER PUBLICATIONS

Weber et al. Formation of cartilage matrix proteins by BMP-transfected murine mesenchymal stem cells encapsulated in a novel class of alginates. Biomaterials, 2002, vol. 23, pp. 203-213.*
Krampera et al. Mesenchymal stem cells for bone, cartilage, tendon and skeletal muscle repair. Bone, 2006, vol. 39, pp. 678-683.*
Murphy et al. Stem Cell Therapy in a Caprine Model of Osteoarthritis. Arthritis Rheumatism, 2003, vol. 48, pp. 3464-3474.*
Ali et al. Addition of human mesenchymal stem cells & osteogenic protein-1 to demineralised bone matrix and insoluble collagenous matrix results in de novo bone formation. European Cells Materials, 2002, vol. 4, Suppl. 2, pp. 127-128.*
Croitoru-Lamoury et al. Human Mesenchymal Stem Cells Constitutively Express Chemokines and Chemokine Receptors That Can Be Upregulated by Cytokines, IFN-alpha, and Copaxone. J. Interferon Cytokine Res., 2007, vol. 27, pp. 53-64.*
Understanding Stem Cells, National Academy of Sciences, The National Acadamies, National Acadmies Press, 2011.*
Practical Pain Management, vol. 8, Issue 1, Jan. 2008 to Feb. 2008, pp. 12-26.
The American Journal of Sports Medicine, vol. 35, No. 2, pp. 245-251, 2007 (published online in 2006).
Eur Surg Res, 39: 199-207, 2007.
The American Journal of Sports Medicine 34:11, pp. 1774-1778, (originally published in 2006).
Foster, et al., Am. J. Sports Med. 37(11):2259-72 (2009).
Sanchez, et al., Med. Sci. Sports Exerc. 35 (10):1648-52 (2003).
Iwata, et al., Muscle & Nerve 34 (5):623-30 (2006).
Erickson, et al., Biochem. & Biophys. Res. Comm. 290:763-9 (2002).
Sen, et al., J. Cell. Biochem. 81:312-19 (2001).
Burris, et al., Mol Endocrinol. 13:410-7 (1999).
Halvorsen, et al., Metabolism 50:407-413 (2001).
Friedenstein, et al., J. Embryol. Exp. Morphol. 16:381-90 (1966).
Bruder, et al., J. Cell Biochem. 64:278-294 (1997).
Bianco, et al., Stem Cells 19:180-92 (2001).
Jones, et al., Arthr. Rheumat. 50:817-27 (2004).
Waymouth, C., Cell Culture Methods for Molecular and Cell Biology, vol. 1, Barnes et al., eds. (1984 New York).
Wu Wei ; Chen Fulin; Liu Yanpu; Ma Qin; Mao Tianqiu: "Autologous injectable tissue-engineered cartilage by using platelet-rich plasma: experimental study in a rabbit model." vol. 65, No. 10, Oct. 2007, pp. 1951-1957, XP 022246768.
Elizaveta Kon et al: "Platelet-rich plasma: intra-articular knee injections produced favorable results on degenerative cartilage lesions", vol. 18, No. 4, Oct. 17, 2009, pp. 472-479, XP 019797696.
Alsousou J et al: "The biology of platelet-rich plasma and its application in trauma and orthopaedic surgery: a review of the literature", vol. 91, No. 8, Aug. 1, 2009, pp. 987-996, XP 009145933.
Michael J Gardner et al: "The efficacy of autologous platelet gel in pain control and blood loss in total knee arthroplasty; an analysis of the haemoglobin, norcotic requirement and range of motion" vol. 31, No. 3, Jul. 1, 2006, pp. 309-313, XP 019514225.
Castro-Malaspina et al., Atherosclerosis, 56(20); 289-301 (1980).
Castro-Malaspina et al., Myelofibrosis and Biology of Connective Tissue, 209-236 (1984).
Castro-Malaspina et al., Blood, 59(5); 1046-1054 (1982).
Mesoblast: the adult stem cell company, Announcement, 2 pages (2008).

(Continued)

*Primary Examiner* — Deborah Crouch
(74) *Attorney, Agent, or Firm* — Lerner, David, Littenberg, Krumholz & Mentlik, LLP

(57) ABSTRACT

Disclosed are methods of enhancing recovery from joint surgery, comprising administering to the joint during surgery a composition comprising stem or progenitor cells in an amount effective to enhance recovery, and a pharmaceutically acceptable carrier.

21 Claims, No Drawings

OTHER PUBLICATIONS

The Adult Stem Cell, 1-41 (2001).
Stem Cells and Bone Growth Factors: From Experimentation to Clinical Medicine: An Ex Vivo in Vitro Study (2004) http://proceedings.jbjs.org.uk/cgi/content/abstract/87-B/SUPP_II/203-d?e.
Osteoarthritis and Cartilage, vol. 16, Supp. 4, pp. S44 and S54, (2008).
"Neochondrogenesis and the Role of Stem Cells: An Experimental Study in a Goat Model (E-94)", E-Poster (E-94), 5th International European Federation of National Associations of Orthopaetic Sports Traumatology (EFOST) Congress Nov. 26-29, 2008, Turkey.
Saw, Khay-Yong, "A novel approach to Neocondrogenesis induced by Peripheral Blood Stem Cells and Hyaluronic Acid", E-Poster (E95), 5th International European Federation of National Associations of Orthopaetic Sports Traumatology (EFOST) Congress Nov. 26-29, 2008, Turkey.

* cited by examiner

ADMINISTRATION OF STEM OR PROGENITOR CELLS TO A JOINT TO ENHANCE RECOVERY FROM JOINT SURGERY

CROSS-REFERENCE TO RELATED APPLICATIONS

This application claims the benefit of the filing date of U.S. Provisional Patent Application No. 61/199,242 filed Nov. 14, 2008, the disclosure of which is hereby incorporated herein by reference.

BACKGROUND OF THE INVENTION

Different techniques are known in the art for promoting healing of joints following surgery. Platelets are one such agent for this purpose. Platelets secrete a number of factors including serotonin, fibronectin, ADP, thromboxane A, platelet factor 4, platelet-derived growth factor, and platelet activating factor. Release of these factors is believed to cause a chemotactic response which initiates the process of migration between endothelial cells. As more factors continue to be released from platelets as well as monocytes and macrophages, angiogenesis, osteogenesis and the formation of granulation tissue are promoted. Several platelet-based products are commercialized under the labeling of Platelet Rich Plasma (PRP), also referred to as Autologous Platelet Gel. The commercial products include the GPS® System (Biomet), Fibrinet (Cascade Medical), and SmartPrep (Harvest), which are described for use following arthroscopic repairs, such rotator cuff repair, meniscus repair, and ACL reconstruction. These PRP systems are disclosed as containing several growth factors, including vascular endothelial growth factor, platelet-derived growth factor, transforming growth factor-β, fibroblast growth factor and epidermal growth factor.

Iwata, et al., Muscle & Nerve 34(5):623-30 (2006), reports use of fibroblast growth factor-2 to enhance functional recovery of reinnovated muscle, e.g., following surgery.

Sanchez, et al., Med. Sci. Sports Exerc. 35(10):1648-52 (2003), reports the application of an autologous plasma rich in growth factors as being beneficial in restoring connective tissues following arthroscopic treatment of large, non-traumatic avulsions of articular cartilage in the knee.

Foster, et al., Am. J. Sports Med. 37(11):2259-72 (2009), is a review that reports on the use of Platelet-rich plasma for chronic tendinopathy, bone healing, acute ligamentous injuries, total knee arthroplasty, ACL reconstruction, acute achilles tendon repair, rotator cuff repair, acute cartilage and meniscus repair.

SUMMARY OF TEE INVENTION

An aspect of the present invention is directed to a method for expediting recovery from joint surgery. The method entails administering to the joint, during the course of surgery, a composition containing allogeneic or autologous progenitor cells, embryonic or adult stem cells, and a pharmaceutically acceptable carrier. The composition may be administered directly to the joint during the course of i.e., as an adjunct to surgery. Typically, the administration of the composition is the penultimate or last step in a surgical procedure, preferably an endoscopic, arthroscopic, or mini-open procedure, or prior to closure of the surgical incision. The administration may be part of the lavage step executed at the end of the surgery. The administration may be directly into the joint space or the area directly surrounding the joint, such as the synovial fluid of the knee for example.

Another aspect of the present invention is directed to a composition containing allogeneic or autologous embryonic, adult stem cells, or progenitor cells, and a pharmaceutically acceptable carrier. The inventive compositions may further contain other therapeutic agents, such as growth factors, as well as inert ingredients, such as gelling agents, hydrophilic agents, surfactants and phospholipids. The carrier may comprise elements naturally present in the synovial fluid, such as hyaluronans, glucosamine, chondroitin sulfate, aggrecans, and collagen. Thus, it may be used as substitute for or complement to the joint fluid.

The compositions and methods of the present invention may provide for expedited recovery from joint surgery, particularly where the underlying damage is due to injury, inflammation, and/or a disease or disorder such as osteoarthritis. The stem cells may not only differentiate into desired tissue (such as cartilaginous tissue or synoviocytes), they will also recruit the patient's own cells and produce proteins and other beneficial substances such as growth factors, all of which aid in tissue regeneration, repair, stabilization, lubrication, and pain reduction.

DETAILED DESCRIPTION

Embryonic stem cells may be suitable for use in the present invention. A variety of non-embryonic stem cells may also be suitable for use in the present invention, including adult stem cells, and embryonic-like stem cells, such as those isolated from placenta, umbilical cord or umbilical cord blood. Adult stem cells offer significant advantages compared to embryonic stem cells. Since they are naturally quiescent unless stimulated by a signal, they do not have to be kept from differentiating. In some embodiments, the cells are autologous, thus obviating immunorejection. Further, they do not form tumors in vivo.

In a preferred embodiment, these cells are allogeneic. Allogeneic cells when carefully selected and properly manipulated can be immune-privileged and not elicit immunorejection. Allogeneic stem cells derived from bone marrow have been shown to not elicit immunorejection when injected in the joint to treat osteoarthritis. See, Murphy, et al., Arthritis & Rheumatism 48:3464-74 (2003); and "4. The Adult Stem Cell." In Stem Cell Information [World Wide Web site]. Bethesda, Md.: National Institutes of Health, U.S. Department of Health and Human Services, 2009.

The stem cells of the invention are pluripotent, which as used herein means that the cells are capable of differentiating into tissues of all three germ layers—mesoderm, endoderm, and ectoderm. In addition, they are self-renewing, and can remain dormant or quiescent within tissue. Stem cells of the present invention may thus be referred to as "Pluripotent adult stem cells" (PPASCs). PPASCs are present in and can be isolated from a number of relatively accessible tissues, including skeletal muscle, bone marrow, blood, placenta, fat, synovium, periosteum, bone, skin, and musculo-skeletal tissues, including ligament, tendon, cartilage and meniscus. PPASCs may be isolated, maintained and expanded in culture according to procedures known in the art. See, e.g., U.S. Patent Application Publication No. 20050260251.

The mechanism of action of the cells in the joint may involve tissue regeneration via differentiation of these stem cells into tissue-specific cells. Another mechanism of action may involve the secretion of soluble factors and signals from these exogenous stem cells. This secretion may in turn enable, accelerate, and/or enhance a positive biological process that benefits the recovery of the joint. These soluble factors may also play a chemotactic role in attracting circulating cells in the joint or in the vicinity of the joint. The stem cells of the present invention may also be multipotent, which as used herein, refers to stem cells that are capable of differentiating into tissues of multiple origins but not all three germ layers.

Adipose tissue offers yet another source of multipotent stromal or adult stem cells that may be suitable for use in the present invention. It has been demonstrated that human adipose tissue-derived stem cells can differentiate along the adipocyte, chondrocyte, and osteoblast lineage pathways [Erickson, et al., Biochem. & Biophys. Res. Comm. 290:763-9 (2002); Gronthos, et al., J. Cell Physiol. 189(1):54-63 (2001); Halvorsen, et al., Metabolism 50:407-13 (2001); Halvorsen, et al., Tissue Eng. 7(6):729-41 (2001); Harp, et al., Biochem. Biophys. Res Comm. 281:907-12 (2001); Saladin, et al., Cell Growth & Diff. 10:43-8 (1999); Sen, et al., J. Cell. Biochem. 81:312-19 (2001); Zhou, et al., Biotechnol. Tech. 13:513-7 (1999); Zuk, et al., Tissue Eng. 7:211-28 (2001)].

Adipose tissue is readily accessible and abundant in many individuals. Adipocytes can be harvested by liposuction on an outpatient basis. This is a relatively non-invasive procedure with cosmetic effects that are acceptable to the vast majority of patients. By "adipose" it is meant any fat tissue. The adipose tissue may be brown or white adipose tissue, derived from subcutaneous, omental/visceral, mammary, gonadal, or other adipose tissue site. Preferably, the adipose is subcutaneous white adipose tissue. Such cells may comprise a primary cell culture or an immortalized cell line. Adipose tissue offers many practical advantages for tissue engineering applications. First, it is abundant. Second, it is accessible to harvest methods with minimal risk to the patient. Third, it is replenishable. While stromal cells represent less than 0.01% of the bone marrow's nucleated cell population, there are up to $8.6 \times 10^4$ stem cells per gram of adipose tissue [Sen, et al., J. Cell. Biochem. 81:312-19 (2001)]. Ex vivo expansion over 2 to 4 weeks yields up to 500 million stem cells from 0.5 kilograms of adipose tissue. These cells can be used immediately or cryopreserved for future autologous or allogeneic applications.

Adipose tissue-derived stem or stromal cells may be isolated and expanded in accordance with standard techniques in the art. See, e.g., Burris, et al., Mol. Endocrinol. 13:410-7 (1999); Erickson, et al., Biochem. & Biophys. Res. Comm. 290:763-9 (2002); Gronthos, et al., J. Cell Physiol. 189(1): 54-63 (2001); Halvorsen, et al., Metabolism 50:407-13 (2001); Halvorsen, et al., Tissue Eng. 7(6):729-41 (2001); Harp, et al., Biochem. Biophys. Res. Commun. 281:907-12 (2001); Saladin, et al., Cell Growth & Diff. 10:43-8 (1999); Sen, et al., J. Cell. Biochem. 81:312-19 (2001); Zhou et al., Biotechnol. Tech. 13:513-17 (1999)]. Adipose tissue-derived stem cells are obtained from minced human adipose tissue by collagenase digestion and differential centrifugation according to known techniques [Halvorsen, et al., Metabolism 50:407 413 (2001); Hauner, et al., J. Clin. Invest. 84:1663-70 (1989); Rodbell, et al., J. Biol. Chem. 241:130-9 (1966)].

Adipose tissue from a variety of sources may be processed to produce stem cells for the generation of a cell possessing at least one genotypic or phenotypic characteristic of a chondrocyte for repair of an articular cartilage defect. The adipose tissue may be from subcutaneous, breast or perirenal sites. Preferably the adipose tissue is subcutaneous. Liposuction surgery or penniculectomy may provide subcutaneous adipose tissue.

Mesenchymal stem cells or bone marrow stromal cells may also be suitable for use in the present invention. The mesenchymal stem cells may be obtained (e.g., from bone marrow aspirate) and expanded in culture by means known to those skilled in the art. See, e.g., U.S. Published Patent Application No. 20020005205. Bone marrow stromal cells are a mixed cell population that generate bone, cartilage, fat, fibrous connective tissue and the reticular network that supports blood cell formation. See, Friedenstein, et al., J. Embryol. Exp. Morphol. 16:381-90 (1966); Friedenstein, et al., Transplantation 6:230-247 (1968); Friedenstein, et al., Cell Tissue Kinet. 3:393-403 (1970); and Owen, J. Cell Science Supp. 10:63-76 (1988). Bone marrow stromal cells have many features that distinguish them from hematopoietic stem cells (ESCs). The two cell types are easy to separate in vitro. When bone marrow is dissociated, and the mixture of cells it contains is plated at low density, the stromal cells adhere to the surface of the culture dish but the ESCs do not. Given specific in vitro conditions, bone marrow stromal cells form colonies from a single cell called the colony forming unit-F [CFU-F]. These colonies may then differentiate as adipocytes or myelosupportive stroma, a clonal assay that indicates the stem cell-like nature of stromal cells. Unlike HSCs, which do not divide in vitro (or proliferate only to a limited extent), bone marrow stromal cells can proliferate for up to 35 population doublings in vitro. See, Bruder, et al., J. Cell Biochem. 64:278-294 (1997). They grow rapidly under the influence of such mitogens as platelet-derived growth factor [PDGF}, epidermal growth factor [EGF], basic fibroblast growth factor (bFGF), and insulin-like growth factor-1 [IGF-1]. See, Bianco, et al., Stem Cells 19:180-92 (2001).

Pluripotent cells suitable for use in the present invention may also be obtained from umbilical cord or umbilical cord blood.

Blood is another source of stem cells suitable for use in the present invention.

The human placenta is yet another source of stem cells suitable for use in the present invention. For example, U.S. Pat. No. 7,311,905 and U.S. Patent Publication 20040048372 teach that the human placenta is rich in several different types of non-embryonic stem cells, including embryonic-like stem cells. As used herein, the term "embryonic-like stem cell" refers to a cell that is not derived from the inner cell mass of a blastocyst. An embryonic-like stem cell is preferably pluripotent. However, the stem cells which may be obtained from the placenta include embryonic-like stem cells, multipotent cells, and committed progenitor cells. Embryonic-like stem cells derived from the placenta may be collected from the isolated placenta once it has been exsanguinated and perfused for a period of time sufficient to remove residual cells. As used herein, the term "placental stem cell" is derived from a postpartum perfused placenta.

As disclosed in U.S. Patent Publication 2004004372, a human placenta is recovered shortly after its expulsion after birth and, in certain embodiments, the cord blood in the placenta is recovered. The placenta may be subjected to a conventional cord blood recovery process. Cord blood recovery may be obtained from several commercial sources, e.g., LifeBank Inc. (Cedar Knolls, N.J.), ViaCord, Cord Blood Registry and Cryocell. The cord blood can be drained shortly after expulsion of the placenta. Postpartum, the placenta is drained of cord blood, and then stored under sterile conditions at either room temperature or at a temperature of 5° C. to 25° C. The placenta may be stored for a period of longer than 48 hours, and preferably for a period of 4 to 24 hours prior to perfusing the placenta to remove any residual cord blood.

Typically, a placenta is transported from the delivery or birthing room to another location, e.g., a laboratory, for recovery of the cord blood and/or drainage and perfusion. The placenta may be transported in a sterile, thermally insulated transport device (maintaining the temperature of the placenta between 20° C.-28° C.), for example, by placing the placenta, with clamped proximal umbilical cord, in a sterile zip-lock plastic bag, which is then placed in an insulated container. The placenta is delivered to the laboratory typically 4 to 24 hours following delivery.

The placenta may be recovered after expulsion under aseptic conditions, and stored in an anticoagulant solution at a temperature of 5° C.-25° C. Suitable anticoagulant solutions heparin (e.g., 1% w/w in 1:1000 solution) and warfarin sodium. The drained placenta is typically stored for no more than 36 hours before the embryonic-like stem cells are collected. The solution which is used to perfuse the placenta to remove residual cells can be the same solution used to perfuse and culture the placenta for the recovery of stem cells. Any of these perfusates may be collected and used as a source of embryonic-like stem cells.

In certain embodiments, the proximal umbilical cord is clamped, preferably within 4-5 cm of the insertion into the placental disc prior to cord blood recovery. In other embodiments, the proximal umbilical cord is clamped after cord blood recovery but prior to further processing of the placenta. Conventional techniques for the collection of cord blood may be used. Typically a needle or cannula is used, with the aid of gravity, to drain cord blood from (i.e., exsanguinate) the placenta. See, U.S. Pat. Nos. 5,192,553; 5,004,681; 5,372,581; and 5,415,665. The needle or cannula is usually placed in the umbilical vein and the placenta is gently massaged to aid in draining cord blood from the placenta.

In some embodiments, the placenta is recovered from a patient by informed consent and a complete medical history of the patient prior to, during and after pregnancy is also taken and is associated with the placenta. These medical records can be used to coordinate subsequent use of the placenta or the stem cells harvested therefrom. For example, the human placental stem cells can then easily be used for personalized medicine for the infant in question, the parents, siblings or other relatives. The human placental stem cells are more versatile than cord blood.

The placenta may be exsanguinated and perfused with a suitable aqueous perfusion fluid, such as an aqueous isotonic fluid in which an anticoagulant is dissolved. Suitable aqueous isotonic fluids for perfusion include, e.g., a 0.9N sodium chloride solution. The perfusion fluid may contain the anticoagulant at a concentration that is sufficient to prevent the formation of clots of any residual cord blood, e.g., of from 1 to 100 units or from 1 to 10 units of heparin per ml. Apoptosis inhibitors, such as free radical scavengers, in particular oxygen free-radical scavengers, can be used during and immediately after exsanguinations. Then these agents can be washed from the placenta. The isolated placenta may be stored under hypothermic conditions in order to prevent or inhibit apoptosis.

The placenta may be exsanguinated by passage of the perfusion fluid through either or both of the umbilical artery and umbilical vein, using gravity flow into the placenta. The placenta may be oriented (e.g., suspended) in such a manner that the umbilical artery and umbilical vein are located at the highest point of the placenta. The umbilical artery and the umbilical vein may be connected simultaneously to a pipette that is connected via a flexible connector to a reservoir of the perfusion fluid. The perfusion fluid is passed into the umbilical vein and artery and collected in a suitable open vessel from the surface of the placenta that was attached to the uterus of the mother during gestation. The perfusion fluid may also be introduced through the umbilical cord opening and allowed to flow or perculate out of openings in the wall of the placenta which interfaced with the maternal uterine wall.

The proximal umbilical cord may be clamped during perfusion, e.g., within 4-5 cm (centimeter) of the cord's insertion into the placental disc.

A sufficient amount of perfusion fluid is used that will result in removal of all residual cord blood and subsequent collection or recovery of placental cells, including but not limited to embryonic-like stem cells and progenitor cells, that remain in the placenta after removal of the cord blood.

When perfusion fluid is first collected from a placenta during the exsanguination process, the fluid may be colored with residual red blood cells of the cord blood. The perfusion fluid tends to become clearer as perfusion proceeds and the residual cord blood cells are washed out of the placenta. Generally from 30 to 100 ml of perfusion fluid are adequate to exsanguinate the placenta and to recover an initial population of embryonic-like cells from the placenta, but more or less perfusion fluid may be used depending on the observed results.

After exsanguination and a sufficient time of perfusion of the placenta, the embryonic-like stem cells should have migrated into the exsanguinated and perfused microcirculation of the placenta where they are collected, such as by washing into a collecting vessel by perfusion. Perfusion of the isolated placenta not only serves to remove residual cord blood but also provide the placenta with the appropriate nutrients, including oxygen. The placenta may be cultivated and perfused with a similar solution which is used to remove the residual cord blood cells, but typically without the addition of anticoagulant agents.

Cells cultured in the placenta may be isolated from the effluent perfusate using standard techniques such as, for example, density gradient centrifugation, magnet cell separation and flow cytometry. In some embodiments, cells collected from the placenta are recovered from the effluent perfusate by centrifugation at 5000×g for 15 minutes at room temperature, which separates cells from contaminating debris and platelets. The cell pellets are re-suspended in IMDM serum-free medium containing 2 U/ml heparin and 2 mM EDTA (GibcoBRL, NY). The total mononuclear cell fraction may be isolated using Lymphoprep (Nycomed Pharma, Oslo, Norway) according to the manufacturer's recommended procedure and then re-suspending the mononuclear cell fraction. Cells may be counted using a hemocytometer. Viability may be evaluated by trypan blue exclusion. Isolation of cells may be achieved by "differential typsinization" using a solution of 0.05% trypsin with 0.2% EDTA (Sigma, St. Louis, Mo.). Differential trypsinization is possible because fibroblastoid cells detach from plastic surfaces within about 5 minutes whereas the other adherent populations require more than 20-30 minutes incubation. The detached fibroblastoid cells may be harvested following trypsinization and trypsin neutralization, using Trypsin Neutralizing Solution (TNS, Bio Whittaker). The cells may then be washed in H.DMEM and resuspended in MSCGM.

In other embodiments, the isolated placenta is perfused for a period of time without collecting the perfusate, such that the placenta may be perfused for 2, 4, 6, 8, 10, 12, 20 or 24 hours, or even days before the perfusate is collected.

In yet other embodiments, cells cultured in the placenta bioreactor are isolated from the placenta by physically dissecting the cells away from the placenta. In yet other embodiments, cells cultured in the placenta bioreactor are isolated from the placenta by dissociating the tissues of the placenta or a portion thereof, and recovering the cultured cells by standard cell separation or sorting methods such as density gradient centrifugation, magnet cell separation and flow cytometry.

In some embodiments, perfusion of the placenta and collection of effluent perfusate are repeated once or twice during the culturing of the placenta, until the number of recovered nucleated cells falls below 100 cells/ml. The perfusates are pooled and subjected to light centrifugation to remove platelets, debris and de-nucleated cell membranes. The nucleated cells are then isolated by Ficoll-Hypaque density gradient centrifugation and after washing, resuspended in H.DMEM. For isolation of the adherent cells, aliquots of 5–10×10$^6$ cells are placed in each of several T-75 flasks and cultured with commercially available Mesenchymal Stem Cell Growth Medium (MSCGM) obtained from Bio Whittaker, and placed in a tissue culture incubator (37° C., 5% $CO_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

In other embodiments, the cells collected from the placenta are cryopreserved for use at a later time. Methods for cryopreservation of cells, such as stem cells, are well-known in the art. See, for example, U.S. Pat. No. 5,192,553 and WO 00/73421.

Embryonic-like stem cells obtained from the placenta may include pluripotent cells, i.e., cells that have complete differentiation versatility, that are self-renewing, and can remain dormant or quiescent within tissue. The stem cells which may be obtained from the placenta include embryonic-like stem cells, multipotent cells, committed progenitor cells, and fibroblastoid cells.

The first collection of blood from the placenta is referred to as cord blood which contains predominantly CD34+ and CD38+ hematopoietic progenitor cells. Within the first 24 hours of post-partum perfusion, high concentrations of CD34+ and CD38− hematopoietic progenitor cells may be isolated from the placenta, along with high concentrations of CD34− and CD38+ hematopoietic progenitor cells. After about 24 hours of perfusion, high concentrations of CD34− and CD38− cells can be isolated from the placenta along with the aforementioned cells. The isolated perfused placenta provides a source of large quantities of stem cells enriched for CD34+ and CD38− stem cells and CD34− and CD38+ stem cells. The isolated placenta which has been perfused for 24 hours or more provides a source of large quantities of stem cells enriched for CD34− and CD38− stem cells.

Embryonic-like stem cells are viable, quiescent, pluripotent stem cells that exist within a full-term human placenta and that can be recovered following successful birth and placental expulsion, resulting in the recovery of as many as one billion nucleated cells, which yield 50-100 million multipotent and pluripotent stem cells.

The human placental stem cells provided by the placenta are referred to as embryonic-like, for example, in that they possess (i.e., shown by the designation "+" or lack, as shown by the designation "−") the following cell surface markers have been identified for these cells: SSEA3−, SSEA4−, OCT-4+ and ABC-p+. The embryonic-like stem cells useful in the present invention may be characterized by the presence of OCT-4+ and ABC-p+ cell surface markers. Thus, the invention encompasses use of stem cells which have not been isolated or otherwise obtained from an embryonic source but which can be identified by the following markers: SSAE3−, SSAE4−, OCT-4+ and ABC-p+. The human placental stem cells do not necessarily express MEC Class 2 antigens.

Placental embryonic-like stem cells useful in the present invention may thus be identified by the presence of the following cell surface markers: OCT-4+ and ABC-pt. Further, the invention encompasses use of embryonic-like stem cells having the following markers: CD10+, CD38−, CD29+, CD34−, CD44+, CD45−, CD54+, CD90+, SH2+, SE3+, SE4+, SSEA3−, SSEA4−, OCT-4+, and ABC-p+. The presence of these cell surface markers is routinely determined according to methods such as flow cytometry followed by washing and staining with an anti-cell surface marker antibody. For example, to determine the presence of CD-34 or CD-38, cells may be washed in PBS and then double-stained with anti-CD34 phycoerythrin and anti-CD38 fluorescein isothiocyanate (Becton Dickinson, Mountain View, Calif.).

In another embodiment, cells cultured in the placenta bioreactor are identified and characterized by a colony forming unit assay, which is commonly known in the art, such as Mesen Cult™. medium (stem cell Technologies, Inc., Vancouver, BC)

Embryonic-like stem cells may also be further cultured after collection from the placenta using methods well known in the art, for example, by culturing on feeder cells, such as irradiated fibroblasts, obtained from the same placenta as the embryonic-like stem cells or from other human or nonhuman sources, or in conditioned media obtained from cultures of such feeder cells, in order to obtain continued long-term cultures of embryonic-like stem cells. The embryonic-like stem cells may also be expanded, either within the placenta before collection from the placental bioreactor or in vitro after recovery from the placenta. In certain embodiments, the embryonic-like stem cells to be expanded are exposed to, or cultured in the presence of, an agent that suppresses cellular differentiation. Such agents are well-known in the art and include human Delta-1 and human Serrate-1 polypeptides (see, U.S. Pat. No. 6,337,387), leukemia inhibitory factor (LIF) and stem cell factor. Methods for the expansion of cell populations are also known in the art (see e.g., U.S. Pat. Nos. 6,326,198 and 6,338,942).

Placental-derived embryonic-like stem cells may be assessed for viability, proliferation potential, and longevity using standard techniques known in the art, such as typan blue exclusion assay, fluorescein diacetate uptake assay propidium iodide uptake assay (to assess viability); and thymidine uptake assay, MTT cell proliferation assay (to assess proliferation). Longevity may be determined by methods well known in the art, such as by determining the maximum number of population doubling in an extended culture.

In certain embodiments, the differentiation of stem cells or progenitor cells that are cultivated in the exsanguinated, perfused and/or cultured placenta is modulated using an agent or pharmaceutical compositions comprising a dose and/or doses effective upon single or multiple administration, to exert an effect sufficient to inhibit, modulate and/or regulate the differentiation of a cell collected from the placenta. Agents that can induce stem or progenitor cell differentiation are well known in the art and include $Ca^{2+}$, EGF, α-FGF, β-FGF, PDGF, keratinocyte growth factor (KGF), TGF-β, cytokines (e.g., IL-1-α, IL-1-β, IFN-γ, and TFN), retinoic acid, transferrin, hormones (e.g., androgen, estrogen, insulin, prolactin, triiodothyronine, hydrocortisone, and dexamethasone), sodium butyrate, TPA, DMSO, NMF, DMF, matrix elements (e.g., collagen, laminin, heparan sulfate, and Matrigel™), and combinations of two or more thereof.

Agents that suppress cellular differentiation are disclosed above.

The agent used to modulate differentiation can be introduced into the placental bioreactor to induce differentiation of the cells being cultured in the placenta. Alternatively, the agent can be used to modulate differentiation in vitro after the cells have been collected or removed from the placenta.

Determination that a stem cell has differentiated into a particular cell type may be accomplished by methods well-known in the art, e.g., measuring changes in morphology and cell surface markers using techniques such as flow cytometry or immunocytochemistry (e.g., staining cells with tissue-specific or cell-marker specific antibodies), by examination of the morphology of cells using light or confocal microscopy, or by measuring changes in gene expression using techniques well known in the art, such as PCR and gene-expression profiling.

The cells for use in the present invention may further be manipulated prior to administration to enhance their performance and efficacy in the joint environment once administered. The cells may be "primed" or pre-challenged during the manipulation to simulate the hostile joint environment into which they will be placed. As the joint is likely to be exposed to inflammatory processes, one preferred embodiment is to pre-challenge the cells in an inflammatory environment, for example in the presence of IL-1β, IL-1β converting enzyme, or TNF-α, or other inflammatory cytokines or compounds. Another preferred embodiment is to pre-challenge the cells for use in the present invention in the presence of enzymes commonly present in operated joints or diseased joints. Such proteolytic enzymes include aggrecanase, collagenase, caspases, and MMPs (matrix metalloproteinases).

Another embodiment relates to treat the cells for use in the present invention so that they can preferentially target specific tissue or tissues, a process also referred as homing. The treatment may include using a specific peptide, or peptides, or molecule that binds to the cells being administered, with one active segment being specific to binding to a specific tissue or specific tissues of the joint. A preferred embodiment would be to treat the cells so they home onto synovial tissue. Another preferred embodiment would be to treat the cells so they home onto articulating cartilage and/or firbocartilage (meniscus) tissue.

The cells for use in the present invention may be genetically manipulated prior to use, so they are transfected for growth factors, cytokine, or extra-cellular matrix compounds over-expression using gene therapy technologies. Examples of growth factors include BMPs (e.g., BMP-7), TGF-β, IGF1, β-FGF, and cartilage matrix oligomeric protein. Examples of cytokines include IL-1 receptor antagonist and other interleukin cytokines. Examples of extra-cellular compounds include hyaluronan and collagen.

Once expanded in culture, the stem cells or progenitor cells are formulated into a composition including a pharmaceutically acceptable carrier for administration to the surgical area. The selection of a suitable carrier is within the skill of the ordinary artisan. Representative examples include plasma (autologous and allogeneic), serum (autologous and allogeneic), water for injection, hyaluronan, chemically modified hyaluronan, saline, phosphate buffered saline, chondroitin sulfate, glucosamine, mannosamine, proteoglycan, proteoglycan fragments, chitin, chitosan, or other polysaccharide or polymer materials, and combinations of two or more thereof.

Suitable gel and/or gel-forming substances may also be included in the composition. The gel and/or gel-forming substance may contain an adhesive material such as fibrin, collagen or a transglutaminase system, to adhere the gel or formed gel to the tissues surrounding the site of administration. Suitable gels and gel-forming substances include biologically-based polymers such as a collagen solution or fibrous suspension, hyaluronan, chemically modified hyaluronan, chitosan (hydrolysed chitin), and synthetic polymers such as a photopolymerizable end-capped block copolymer of poly(ethylene oxide) and an α-hydroxy acid. The compositions may further contain surfactants (e.g., lubricin, lipids (e.g., glycerols) and phospholipids or surface-active phospholipids (SAPL) (e.g., DPPC, PLPC, POPC, SLPC, and combinations thereof), and combinations of two or more thereof.

The compositions may further include other non-cellular therapeutically beneficial agents such as growth factors (e.g., TGF-β, EGF, FGF, IGF-1, BMP-7 and OP-1, etc.), glycosaminoglycans (GAGs) (e.g., aggrecan, decorin, biglycan, fibromodulin), chemokines and cytokines (e.g., interleukins and interferons) and hydrophilic compounds (e.g., polylysine, chitosan, hyaluronan). Extracellular matrix molecules that bind to growth factors, e.g., heparan sulfate proteoglycans, may advantageously be added to serve as a reservoir for the factors.

Accordingly, the compositions of the present invention may be administered to affected and surgically repaired joints including knee joints, hip joints, shoulder joints, elbow joints, ankle joints, tarsal and metatarsal joints, wrist joints, spine, carpal and metacarpal joints, and the temporal mandibular joint.

The stem or progenitor cells are administered in an amount effective to expedite or accelerate recovery of the joint from surgery. In general, amounts of the stem or progenitor cells for these purposes range generally from about $1 \times 10^4$ to about $1.5 \times 10^8$, preferably from about $1 \times 10^5$ to about $1 \times 10^8$, more preferably from about $1 \times 10^6$ to about $1 \times 10^8$. The cells are typically delivered in a volume of about 5 ml to about 10 ml, via any medically acceptable device for delivering fluids to open surgical areas or wounds. The exact number of cells is dependent upon a variety of factors, including the age, weight, and sex of the patient, the extent and severity of the damage or injury to the joint, or of the disease affecting the joint, the degree of exudation within the joint, the joint space, and other anatomical characteristics that might influence the delivery.

The cells for use in the present invention and their carrier may be administered in the joint via a variety of techniques. One preferred embodiment is to add the cell solution into the last bag for last step lavage at the end of an arthroscopic intervention. Another preferred embodiment is to administer by pouring, squirting, spraying, flowing the cell solution in the joint space prior to closure of the joint.

The timing of the administration during the course of a surgery is not critical, but is typically performed as the penultimate or last step prior to closure of the surgical opening. Another preferred embodiment is to inject the cell solution prior to closing the joint or after the joint is closed at the end of the surgical intervention.

All publications cited in the specification, both patent publications and non-patent publications are indicative of the level of skill of those skilled in the art to which this invention pertains. Any publication not already incorporated by reference herein is herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of enhancing recovery from joint surgery, comprising administering to the joint during surgery to repair the joint a composition comprising stem or progenitor cells in an amount effective to enhance recovery, and a pharmaceutically acceptable carrier.

2. The method of claim 1, wherein said cells are autogolous progenitor or stem cells.

3. The method of claim 1, wherein said cells are allogeneic progenitor or stem cells.

4. The method of claim 1, wherein said cells comprise adult stem cells.

5. The method of claim 4, wherein said adult stem cells comprise placental-derived embryonic-like stem cells.

6. The method of claim 1, wherein said cells comprise mesenchymal stem cells.

7. The method of claim 1, wherein said cells are transfected with a gene encoding a growth factor, cytokine or extracellular matrix compound.

8. The method of claim 1, wherein prior to being administered, said cells are pre-challenged in an inflammatory environment.

9. The method of claim 1, wherein prior to being administered, said cells are homed to specifically bind one or more joint tissues, including synovial tissue, joint capsule, articulating cartilage, fibrocartilage (meniscus) tissue, ligament or tendon tissue.

10. The method of claim 1, wherein said carrier comprises plasma, serum, water for injection, hyaluronan, chemically modified hyaluronan, saline, phosphate buffered saline, chondroitin sulfate, glucosamine, mannosamine, proteoglycan, proteoglycan fragments, chitin, chitosan, or a combination of two or more thereof.

11. The method of claim 1, wherein said composition further comprises a gelling agent, a hydrophilic agent, a surfactant, a lipid, a phospholipid, a surface-active phospholipids, or a combination of two or more thereof.

12. The method of claim 1, wherein said composition further comprises a non-cellular therapeutic agent.

13. The method of claim 12, wherein said agent comprises a growth factor, cytokine, chemokine, hydrophilic compound, or an extracellular matrix compound.

14. The method of claim 12, where said agent is BMP -7.

15. The method of claim 1, wherein said joint is the knee, hip, shoulder, elbow, ankle, tarsal or metatarsal, wrist, spine, carpal or metacarpal, or temporal mandibular joint.

16. The method of claim 1, wherein the surgery is arthroscopic.

17. The method of claim 1, wherein the surgery is endoscopic.

18. The method of claim 1, wherein said composition is administered via injection prior to closing the joint or after the joint is closed.

19. The method of claim 1, wherein the joint is osteoarthritic.

20. The method of claim 1, wherein said composition is administered directly into the joint space.

21. The method of claim 1, wherein said composition is administered into synovial fluid.

* * * * *